United States Patent
Yamada et al.

[19]

[11] Patent Number: 6,036,829
[45] Date of Patent: Mar. 14, 2000

[54] OXYGEN SENSOR

[75] Inventors: Hirokazu Yamada, Nagoya; Takashi Kojima, Kasugai; Makoto Hori, Ogaki; Masahiro Hamaya, Anjo; Minoru Ota, Okazaki, all of Japan

[73] Assignee: Denso Corporation, Kariya, Japan

[21] Appl. No.: 09/020,334

[22] Filed: Feb. 9, 1998

[30] Foreign Application Priority Data

Feb. 10, 1997 [JP] Japan ................................... 9-041489

[51] Int. Cl.⁷ ................................................. G01N 27/407
[52] U.S. Cl. .......................... 204/427; 204/408; 204/428; 156/89; 219/541; 219/544; 219/553
[58] Field of Search ........................ 204/408, 421–429; 205/783.5, 784, 784.5, 785; 219/270, 541, 552, 553, 544

[56] References Cited

U.S. PATENT DOCUMENTS

| | | | |
|---|---|---|---|
| 4,556,780 | 12/1985 | Atsumi et al. | 219/553 |
| 4,563,568 | 1/1986 | Takizawa | 219/544 |
| 4,616,125 | 10/1986 | Oppitz | 219/553 |
| 4,908,156 | 3/1990 | Dalle et al. | 219/553 |
| 4,912,305 | 3/1990 | Tatemasu et al. | 219/553 |
| 5,451,748 | 9/1995 | Matsuzaki | 219/543 |
| 5,554,839 | 9/1996 | Tsuruta et al. | 219/544 |
| 5,644,676 | 7/1997 | Blomberg et al. | 219/553 |
| 5,800,689 | 9/1998 | Hori et al. | 204/428 |

FOREIGN PATENT DOCUMENTS 60-146847  9/1985  Japan .

Primary Examiner—T. Tung
Attorney, Agent, or Firm—Pillsbury Madison & Sutro LLP

[57] ABSTRACT

An oxygen sensor 3 having a heater 2 capable of providing an improved temperature increasing characteristic, while maintaining an increased amount of introduced air and a high production efficiency. The sensor 3 includes a sensor element 1 having an air chamber 100 in which a heater 2 is arranged. The heater 2 has a rectangular cross sectional shape. In order to produce the heater 2, onto a green ceramic sheet, a heater of a predetermined pattern including a plurality of heater sections is printed. Then, to the printed sheet, different ceramic green sheets are applied so as to obtain a laminated body. The laminated body is subjected to a cutting so as to produce an intermediate body in which a heater section is included. The intermediate body is subjected to a firing to obtain a completed heater.

5 Claims, 12 Drawing Sheets

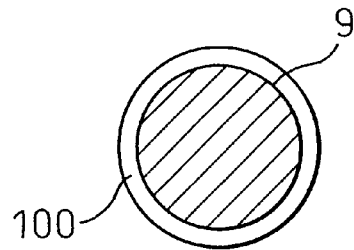
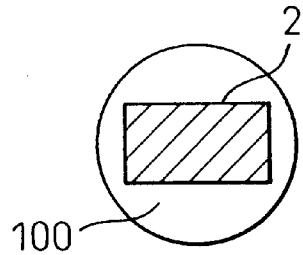
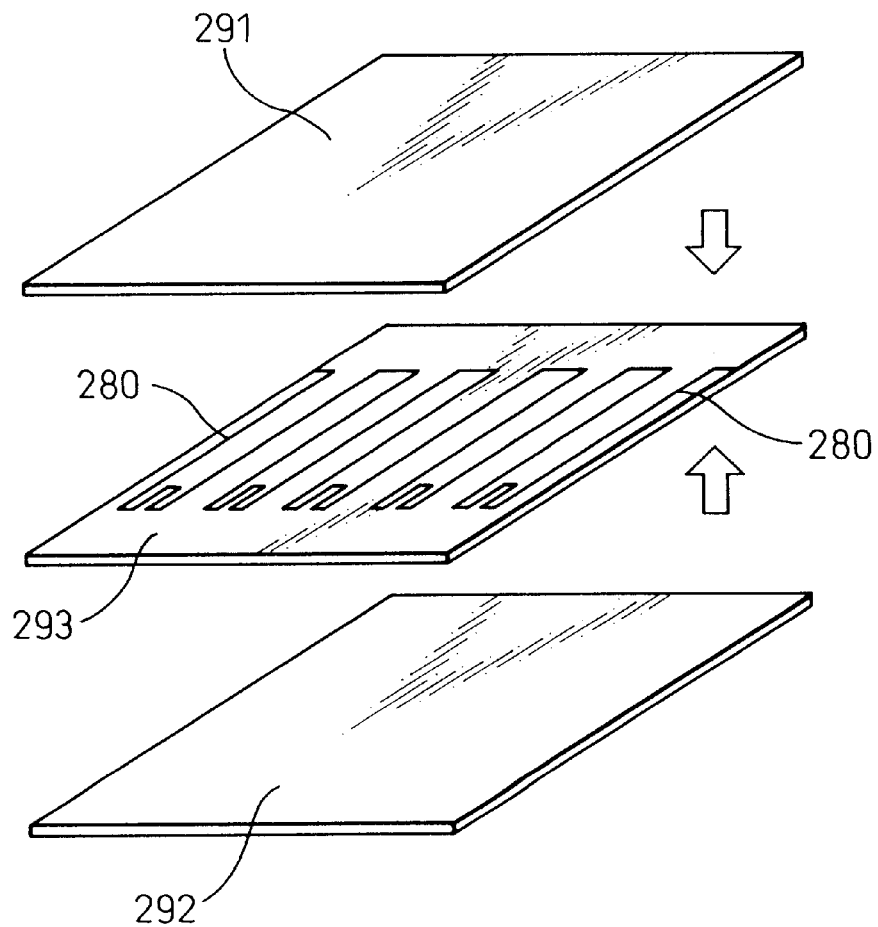

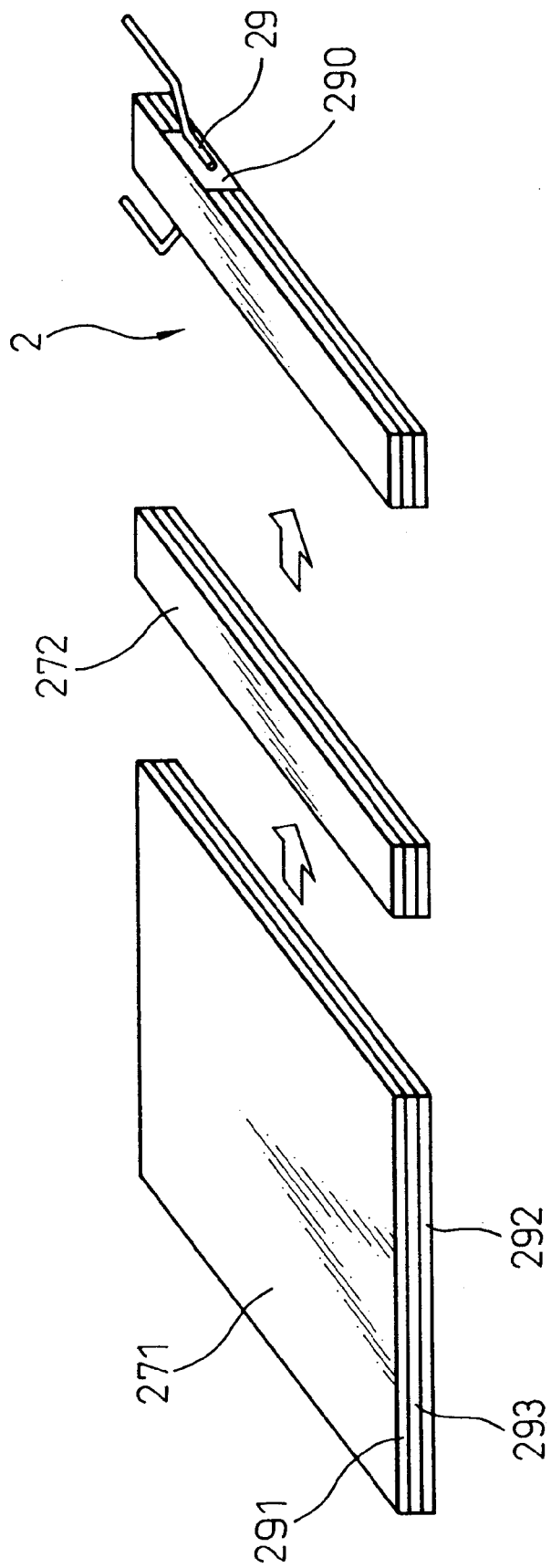

OXYGEN SENSOR

BACKGROUND OF THE INVENTION

1. Field of the Invention

The present invention relates to an oxygen sensor for use in a system, for an internal combustion engine, such as an air fuel ratio control system, and a method for producing such an oxygen sensor.

2. Description of Related Art

In a known air fuel ratio control system for an internal combustion engine, an oxygen sensor is arranged in an exhaust system of the internal combustion engine to detect an air fuel ratio and combustion control is done in accordance with the air fuel ratio detected by the oxygen sensor, so that an increase in a purification efficiency of an exhaust gas is obtained in a three way catalytic converter arranged in an exhaust system of the internal combustion engine.

Such an oxygen sensor includes a detecting element (an oxygen sensor element), which is constructed as a body of a solid electrolyte having oxygen ion conductivity. Namely, the solid electrolyte body is formed as a cup shape, in which an air chamber is formed. Furthermore, the solid electrolyte body forms, at its outer surface, an outer electrode and, at its inner surface, an inner electrode, which is in contact with the air in the air chamber. Furthermore, inside the air chamber, a heater is arranged so that the oxygen sensor element is heated to an activating temperature.

In the prior art structure of the oxygen sensor, as shown in FIG. 16, a heater 9 as rod shape of a circular cross sectional shape is used. The heater 9 is constructed by a heat generating part 21 in which a heat generating element is housed and a supporting section 22 for supporting the heat generating part 21 and for housing lead members 22 electrically connected to the heat generating element in the heat generating part 21.

Now, a method for producing the above construction of the heater 9 will be explained. Namely, as shown in FIG. 17, a ceramic green sheet 90 is subjected to coating with a layer of a desired pattern 200 to be formed into a heat generating element 210 and lead elements 220 by being subjected to a later firing process. Then, on the sheet, a organic binder, which is an ethyl cellulose dissolved in an organic solvent, is painted. Then, the sheet 90 is wrapped around a core rod 900 made of a ceramic material. Then, the core rod 900 together with the sheet 90 wrapped around the rod 900 is subjected to a firing in a furnace of a high temperature in a range between 1400 to 1500° C. Then, at an end of the heater 9, terminal elements 290 are formed so that they are in an electric connection with the lead element 220. Then, lead wires 29 are connected to the terminal elements 290, respectively, by means of a soldering using a soldering material such as AuCu in a vacuum condition at a high temperature in a range between 950 to 1000° C. Finally, the lead wires 29 are connected to an outside electric power source, so that the heat generating element 210 is fed with electric power via the electrode element 220.

In the above mentioned structure in the prior art in FIG. 16, the heater 9 is formed as the rod of a circular cross sectional shape, which, on one hand, causes the value of the cross sectional area to be increased and, on the other hand, causes a loss of the heat to be increased in the upward direction. As a result, the prior art structure of the rod of the circular cross sectional shape is defective in that the speed of the increase in the temperature of the oxygen sensor element is reduced. Furthermore, the circular cross sectional shape of the rod causes the clearance to be small with respect to the faced inner wall of the air chamber, which results in a reduced amount of air introduced into the air chamber, which causes the precision to be reduced in the detection of the oxygen density by the oxygen sensor.

Furthermore, according to the method for producing the heater 9 as briefly explained with reference to FIG. 17, a production efficiency is low due to the fact that a formation of the heater pattern is done on a rod by rod basis.

SUMMARY OF THE INVENTION

An object of the present invention is to provide an oxygen sensor having a heater of an improved temperature increasing characteristic.

Another object of the present invention is to provide an oxygen sensor having a heater which allows an increased amount of air to be introduced into the air chamber.

Still another object of the present invention is to provide a method of producing a heater for an oxygen sensor, capable of a high efficiency.

According to the present invention, an oxygen sensor is provided, comprising:

a cup shaped body made of a solid electrolyte body;

an air chamber inside said solid electrolyte body, which is opened to atmospheric air;

an outer electrode on an outer surface of said solid electrolyte body;

an inner electrode on an inner surface of said solid electrolyte body, and;

a heater including a heat generating part in which a heat generating element is stored and a supporting part for supporting the heat generating portion, the supporting part having a lead element which is in an electric connection with the heat generating element;

a relationship between the cross sectional area Sh of the heat generating part and the cross sectional area Ss of said supporting part being such that $Sh \geq Ss$;

a relationship between the length a of the long side and the length b of the short side in the rectangular cross sectional shape of the heater being such that $0.3 \leq b/a \leq 0.7$.

When the relationship between Ss and Sh is such that Sh<Ss, i.e, the cross sectional area of the supporting part is larger than that of the heat generating part, it may cause a loss of heat to the upper part of the heat onto be increased.

The cross sectional area Sh implies a cross sectional area of a portion of the heater where the heat generating element is embedded as shown in FIGS. 2 and 3. Furthermore, the cross sectional area Ss implies a cross sectional area of a portion of the heater where the lead element is embedded as shown in FIGS. 2 and 3.

A value of b/a larger than 0.7 may cause the temperature increase speed characteristic of the oxygen sensor to be worsened and a clearance between the inner wall of the air chamber of the oxygen sensor and the heater to be reduced, which may cause the amount of air introduced into the air chamber to be too small.

On the other hand, a value of b/a smaller than 0.3 may cause a clearance between the inner wall of the air chamber of the oxygen sensor and the heater to be unnecessarily increased, which causes the size of the oxygen sensor to be increased, which makes it difficult to install the sensor in a small space. Furthermore, the diameter of the heater is reduced, resulting in a reduction in the mechanical strength as well as the durability of the heater. As to practical shapes of the heater, i.e., the arrangement of the long side a and the short side b, refer to FIGS. 4 and 11.

In the construction of the present invention, between the cross sectional area Sh of the heat generating part and the cross sectional area Ss of the supporting part, a relationship Sh≧Ss is obtained. As a result, a loss of heat in the upper direction of the heater is reduced.

Furthermore, in the heater according to present invention, the cross sectional shape of the heater is rectangular. As a result, as shown in FIG. 5, the cross sectional area of the heater insertable into the air chamber of the same diameter is reduced over the case where the cross sectional shape of the heater is of a circular shape. As a result, the amount of the air which is in contact with the heater is reduced, so that a loss of heat, from the upper end of the heater to the atmosphere, is reduced, which results in a more effective heating of the oxygen sensor.

Due to the relationship between the length a of the long side and the length b of the short side in the rectangular cross sectional shape of the heater, which is such that $0.3 \leq b/a < 0.7$, a desirable clearance is maintained in the air chamber, thereby keeping a sufficient amount of the air introduced into the air chamber. As a result, if a large amount of a pumping of the oxygen in the air chamber via the solid electrolyte body occurs, a lack of oxygen in the air chamber does not occur, which makes it always possible to obtain an oxygen measurement of an increased precision.

Due to the reduction in the amount of air contacting the heater, the amount of the heat discharged to the atmosphere from the upper end of the heater is reduced, which allows the oxygen sensor to be more effectively heated. As a result, production of an oxygen sensor of an improved temperature increasing speed characteristic is possible.

In short, according to present invention, the production of an oxygen sensor, having an improving temperature increasing characteristic while keeping a sufficient amount of air introduced into the air chamber and providing an increased production efficiency, is possible.

Preferably, said heater is beveled at its corners of the rectangular cross section. Such a beveling is advantageous in that an occurrence of cracking or damage at the corner portions of the heater is prevented when the heater is assembled to the oxygen sensor.

Preferably, said heater has, at its outer surface, a coating of a high radiation film made of at least one of materials selected from $Fe_2O_3$, $NiO$, $Y_2O_3$ and $Si_3N_4$. Due to the provision of such a high radiation film, the heater is, at the corner portions, formed as a curved shape, which is also advantageous in that an occurrence of cracking or damage at the corner portions of the heater is prevented when the heater is assembled to the oxygen sensor.

Such a high radiation film is made of a material which has a radiation (adsorption) rate which is almost equal to 1.0, which allows the heat to be easily emitted or absorbed. Namely, a provision of such a high radiation film allows the heat of the heater to be effectively absorbed, which results in an effective emission of a heat toward the inner surface of the air chamber of the oxygen sensor. As a result, an oxygen sensor of an improved temperature increasing speed is obtained.

Preferably, in a gap between an inner wall of the air chamber facing the heater and the heat generating part of the heater, a relationship between the distance L1 of said inner wall said from the long side of the rectangular cross section and the distance L2 of said inner wall said from the short side of the rectangular cross section is such that $1.5 \leq L1/L2 \leq 2.5$.

As a result, an oxygen sensor with an improved speed of the temperature increase is obtained. In the case where the ratio L1/L2 is lower than 1.5, it may be possible that the temperature increasing speed is insufficient. Furthermore, a clearance between the inner surface of the air chamber and the heater is reduced, resulting in a lack of introduced air.

Contrary to this, a ratio L1/L2 larger than 2.5 may means that the clearance between the inner wall of the air chamber and the heater is unnecessarily increased, which causes the size of the oxygen sensor to be increased, which makes it difficult for the sensor to be mounted in a limited space. Furthermore, the shape of the heater is thinner, which makes it possible that the mechanical strength or durability of the sensor is reduced.

It should be noted that the distance L1 and L2 are distances on the inner wall of the air chamber from the long side length and the short side length respectively, of a rectangular shape in the cross section of the heater.

Preferably, a relationship between a cross sectional area S1 of the space in the air chamber in which the heater is inserted and the cross sectional area S2 of the heat generating part of the heater is such that $S2/S1 \leq 0.5$.

By this arrangement, an oxygen sensor with an improved temperature increasing speed characteristic is obtained. Namely, when the value of S2/S1 is smaller than 0.5, the temperature increasing speed characteristic of the oxygen sensor is worsened. In this regard, the space area in the air chamber is the cross sectional area of the air chamber minus the cross sectional area of the heat generating part of the heater, which corresponds to the clearance between the inner wall of the air chamber and the heater.

According to the present invention, a process is provided for producing a heater for an oxygen sensor, said heater including a heat generating part in which a heat generating element is stored and a supporting part for supporting the heat generating portion, said process comprising the steps of:

providing a green ceramic sheet;

printing, on said green sheet, a heater material at a predetermined pattern including a plurality of heater sections;

applying a different green ceramic sheet to the ceramic sheet on which said pattern is formed, so as to obtain a laminated sheet body;

cutting the laminated sheet body so as to separate an intermediate body including a heater section, and;

firing the intermediate body.

According to this method, the production efficiency is increased due to the fact that a number of heaters are simultaneously produced. In this regard, the heater pattern corresponds to screen printed portions of electro-conductive material, such as Pt or Pd, which become a heat generating element and a lead after the firing.

BRIEF EXPLANATION OF ATTACHED DRAWINGS

FIG. 5(*a*) is a cross sectional view of a heater in the prior art.

FIG. 5(b) is similar to FIG. 5(a) but illustrates a construction of the present invention.

FIG. 6 is a schematic perspective view illustrating a first step of a method for producing a heater according to the present invention.

FIGS. 7(a) to 7(c) are schematic perspective views illustrating a second step of a method for producing a heater according to the present invention.

Figure 8:
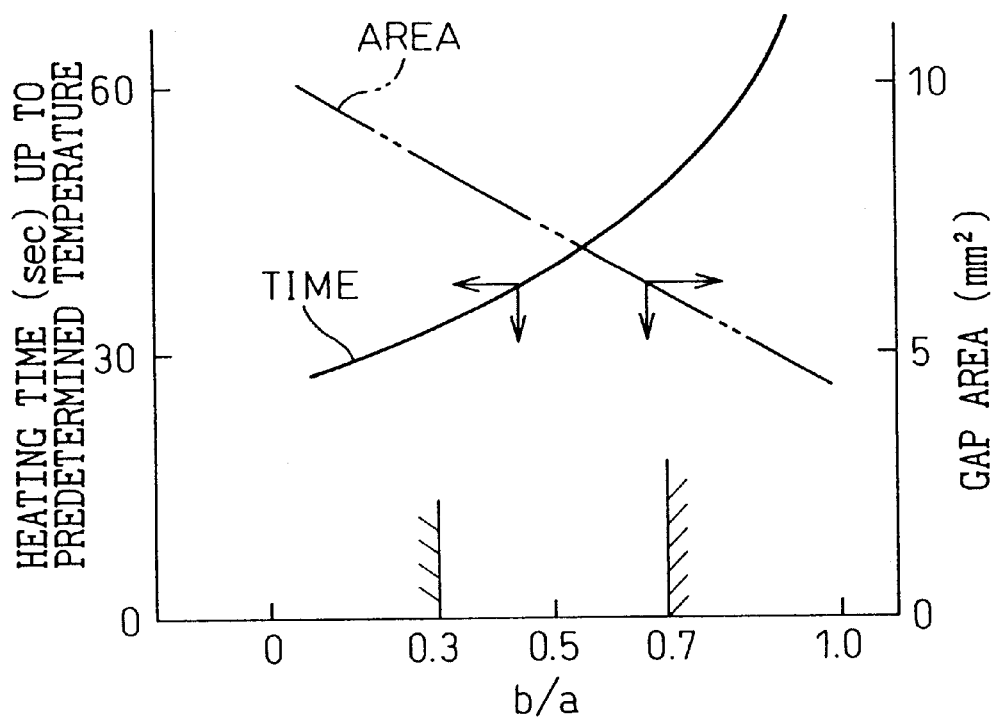

FIG. 8 shows, with respect to a ratio b/a, a gap area in the air chamber and the time for the temperature of the heater to be increased to a predetermined value.

Figure 9:
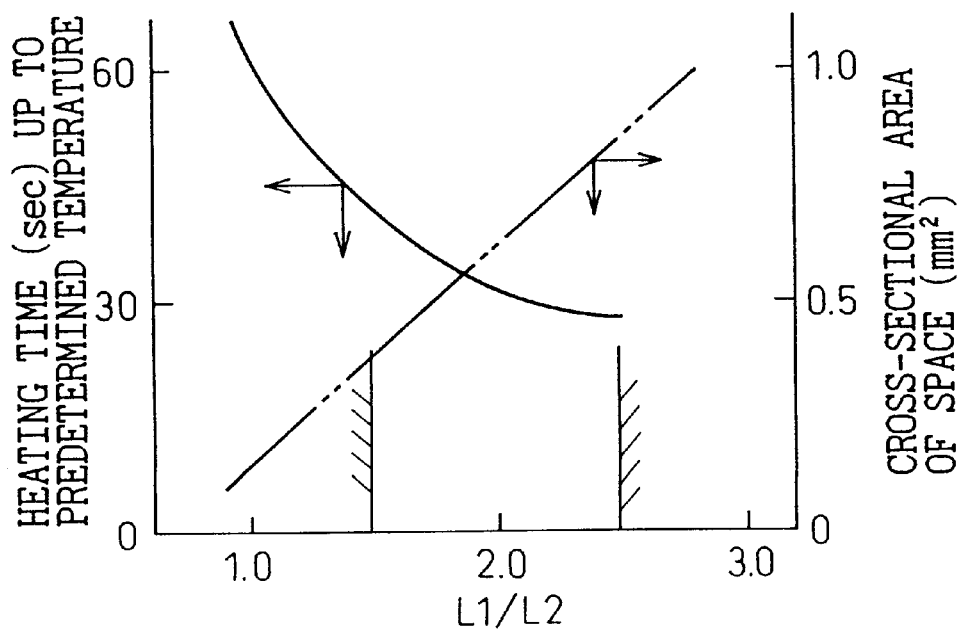

FIG. 9 shows, with respect to a ratio L1/L2, a gap area in the air chamber and the time for the temperature of the heater to be increased to a predetermined value.

Figure 10:
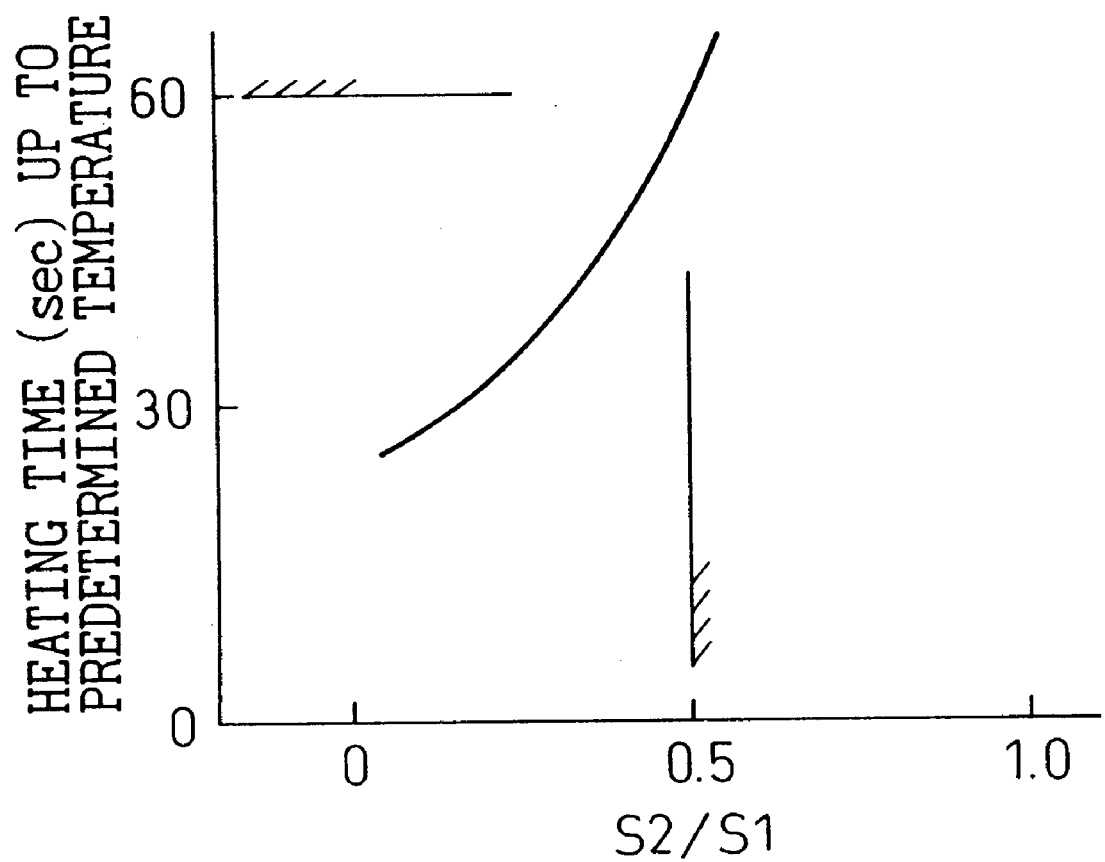

FIG. 10 shows, with respect to a ratio S2/S1, the time for the temperature of the heater to be increased to a predetermined temperature.

FIGS. 11(a) to 11(d) show various cross sectional shapes of a heater.

Figure 12:
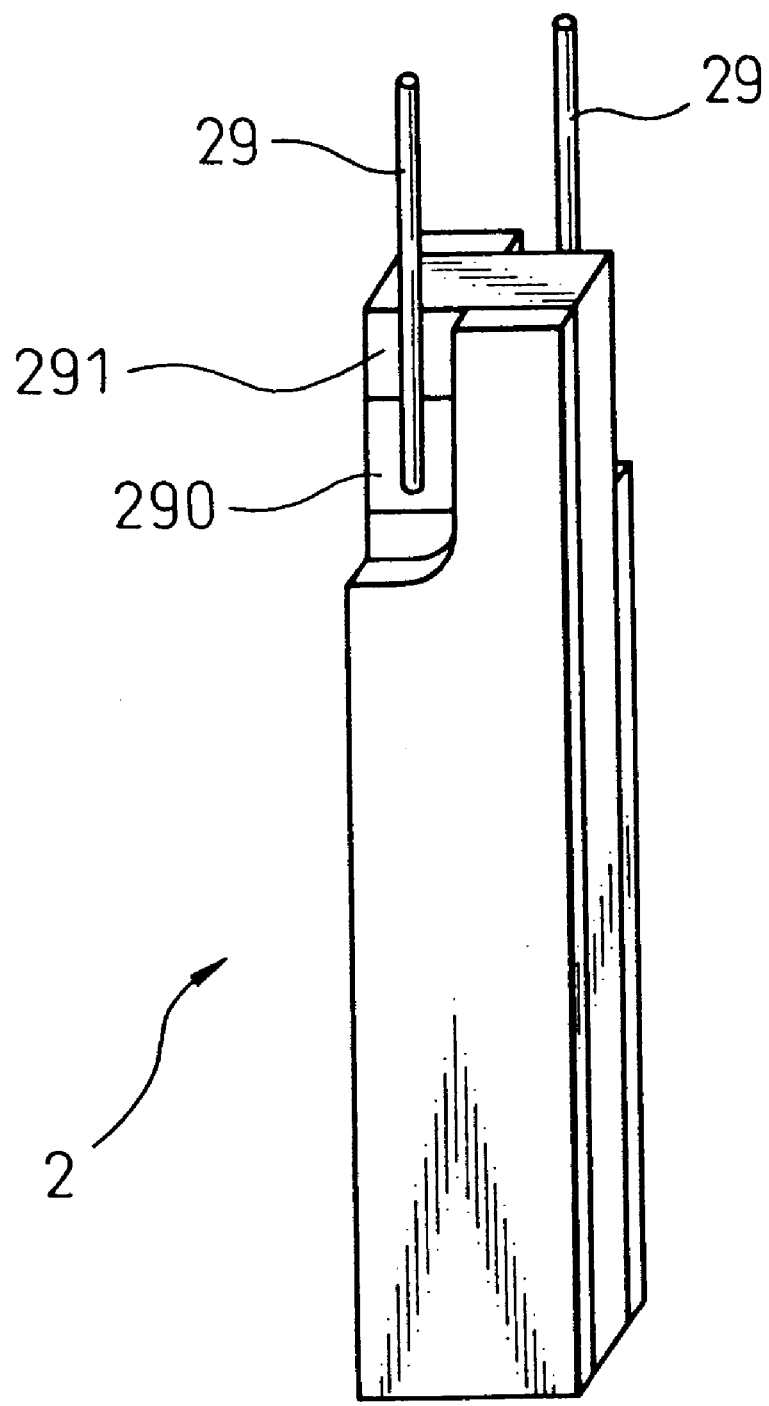

FIG. 12 is a perspective view of a heater in a modified embodiment.

Figure 13:
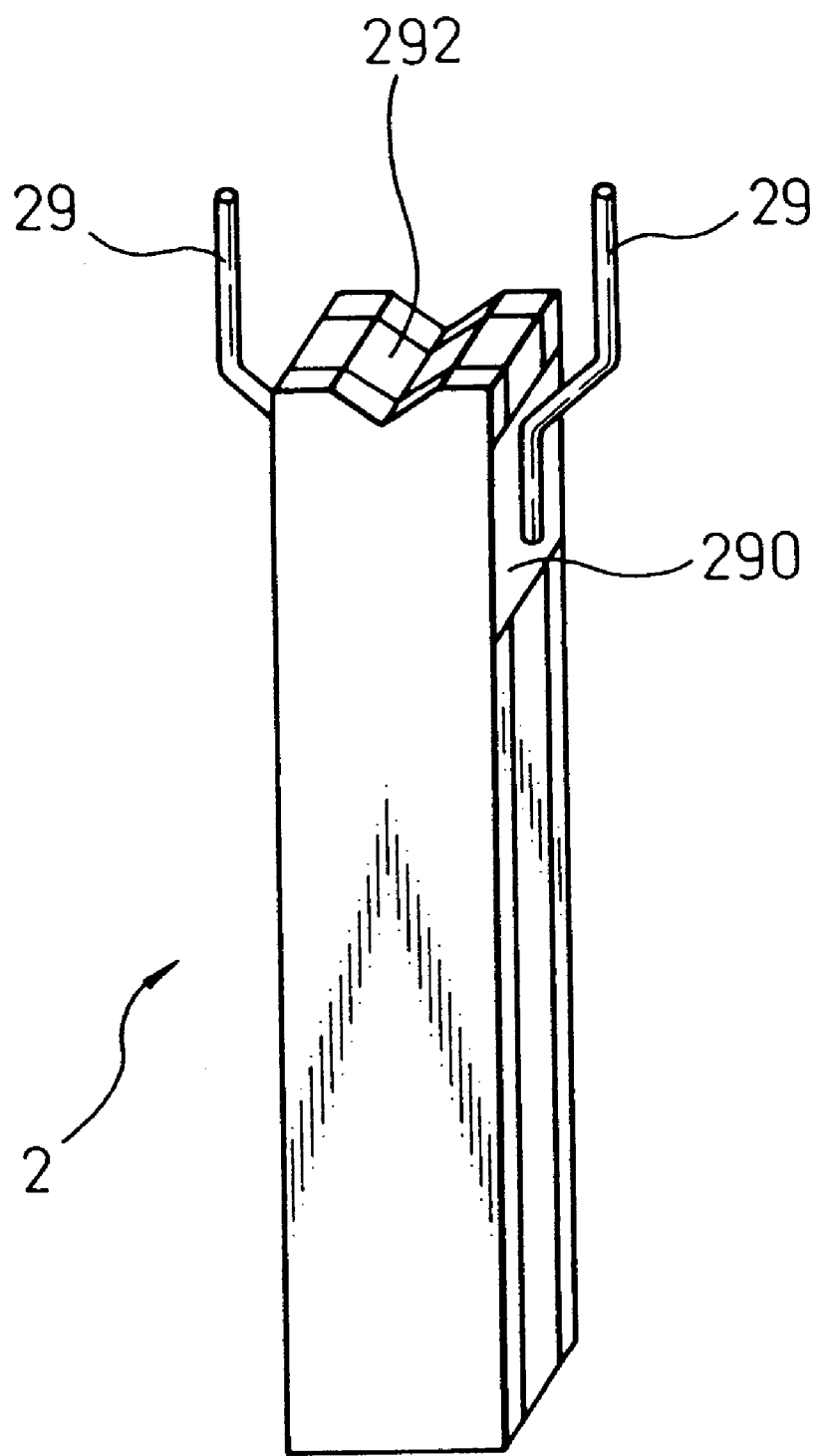

FIG. 13 is a perspective view of a heater in a further modification.

Figure 14:
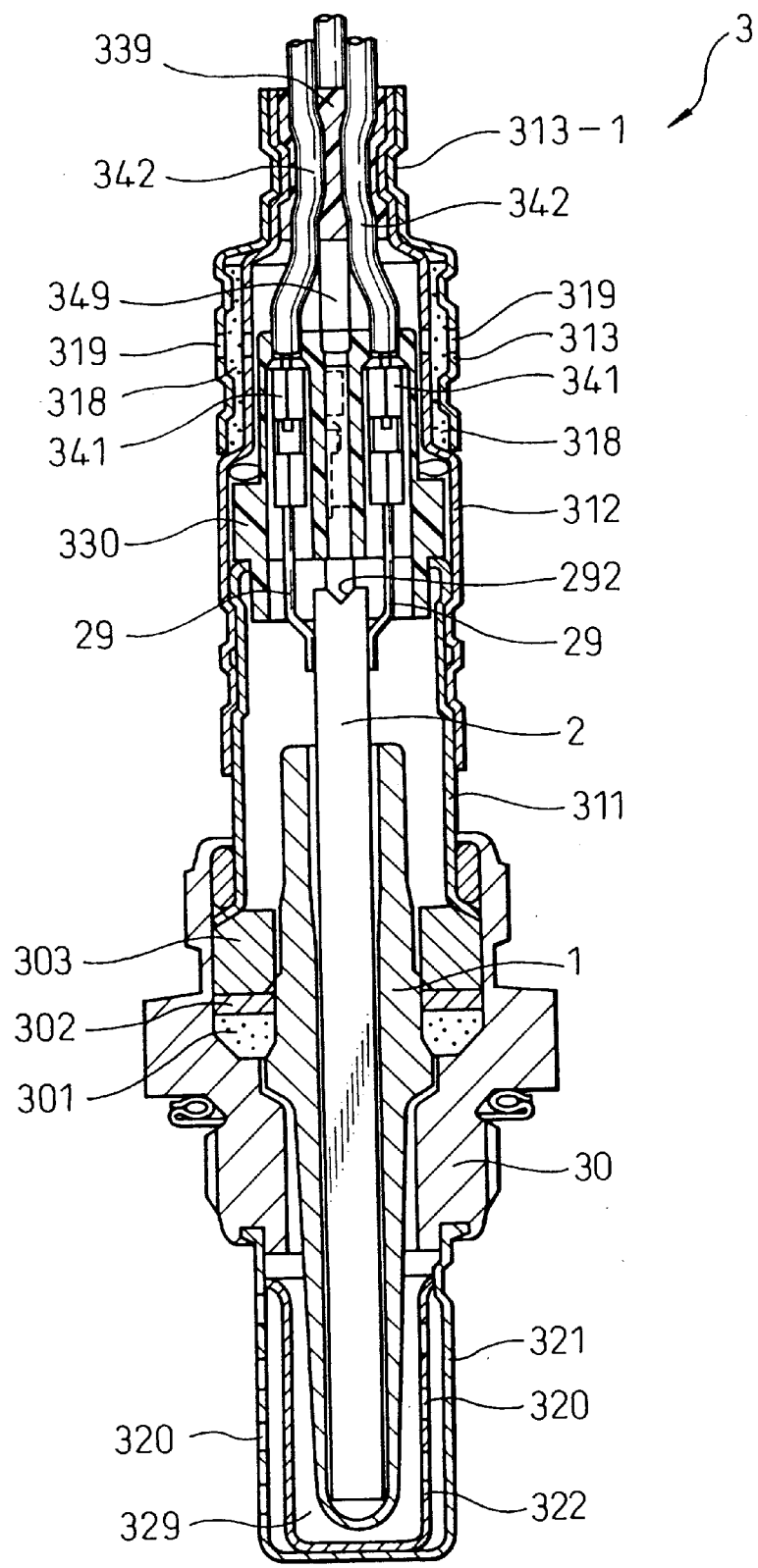

FIG. 14 is a longitudinal cross sectional view of an oxygen sensor.

Figure 15:
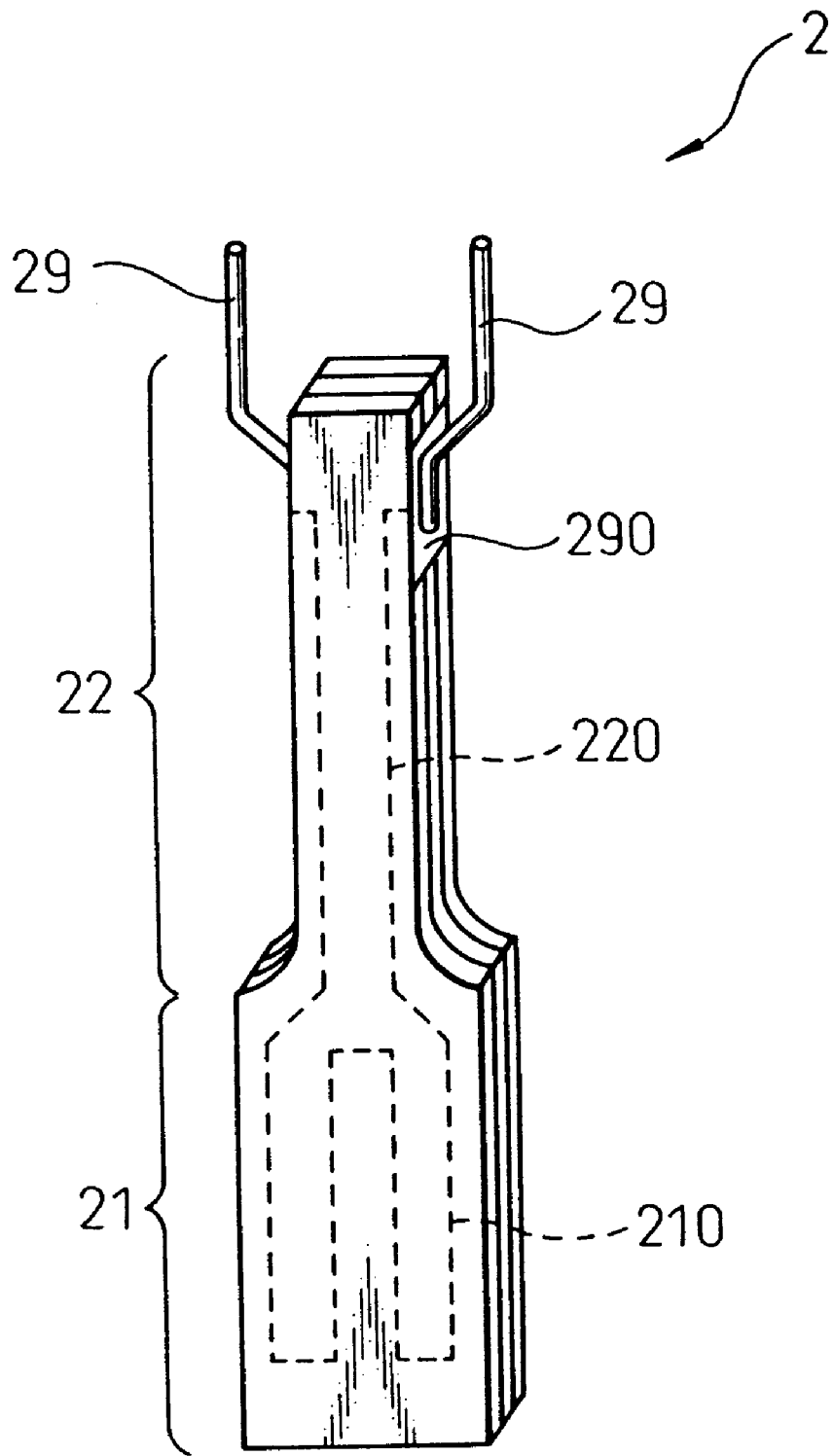

FIG. 15 is a perspective view of a heater in a further another modification.

Figure 16:
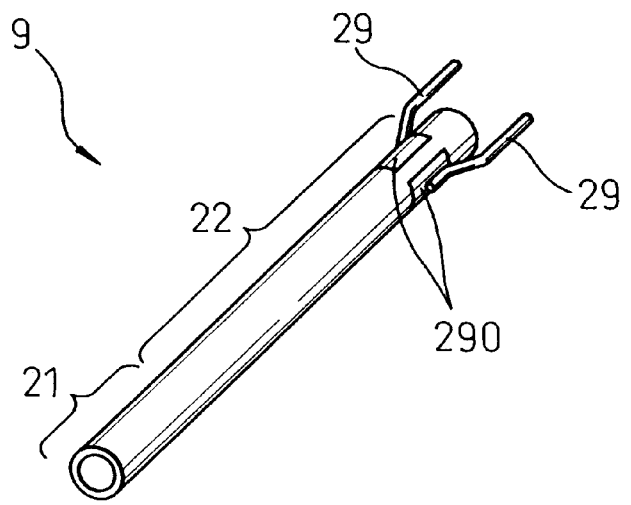

FIG. 16 is a perspective view of a heater in a prior art.

Figure 17:
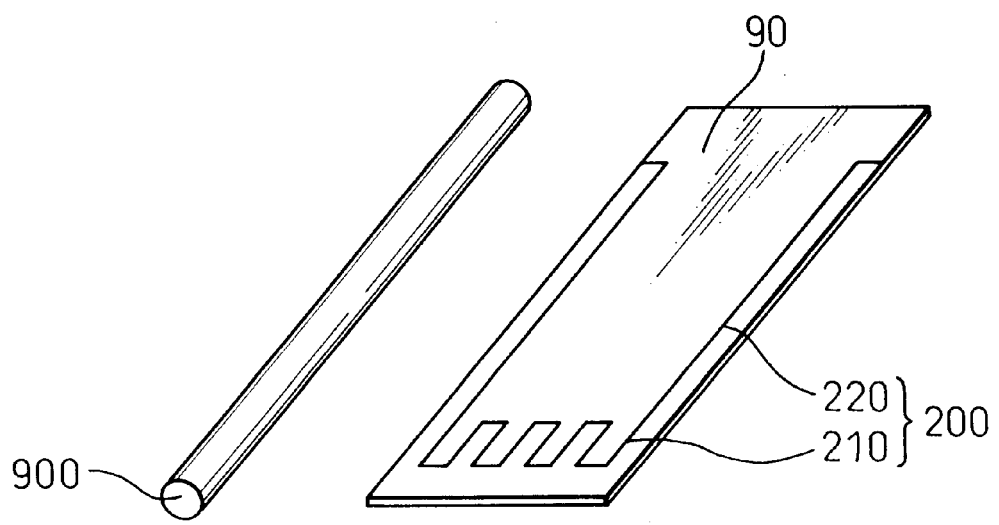

FIG. 17 is a perspective view of a method for producing a heater in FIG. 16.

DESCRIPTION OF PREFERRED EMBODIMENTS

Now, embodiments of the present invention will be explained with reference to the attached drawings.

FIG. 14 is related to a specific embodiment of the present invention directed to supporting a heater as will explained later. However, the remaining general structure as an oxygen sensor is similar to all of the embodiments of the present invention. Thus, a general structure of an oxygen sensor 3 will first be explained with reference to FIG. 14. Namely, the oxygen sensor 3 includes an oxygen sensor element 1 and a heater 2 with lead wires 29. The oxygen sensor element 1 is fixed to a housing 30, which is adapted to be connected to a desired location, such as an exhaust manifold (not shown) of an internal combustion engine (not shown) in an engine compartment of a vehicle.

The oxygen sensor element 1 together with the heater 2 is inserted to the housing 30. A lower cover 311 is fixed to an upper end of the housing 30 via a layer made of talc 301, a ring shaped packing member 302 and an insulator 303. An intermediate cover 312 is inserted to a top end of the lower cover 311, while an insulator 330 is nipped between a top edge of the cover 311 and an inner shoulder portion of the intermediate cover 312. The lead wires 29 of the heater 2 are passed through corresponding holes in the insulator 330 and are connected to ends of outside connecting wires 342 by means of respective connectors 341. The outside connecting wires 342 are passed through respective holes in a rubber bushing 339 fitted to an upper end of the intermediate cover 312. An upper cover 313 is inserted into the intermediate cover 312 and is, at a location 313-1, crimped so that the covers 312 and 313 are connected with each other while the rubber bushing 339 is elastically deformed. A water repellent filter 318 is arranged in an annular space between the intermediate cover 312 and the outer cover 313, which has vent holes 319 opened to the water repellent filter 318.

First Embodiment

Figure 1:
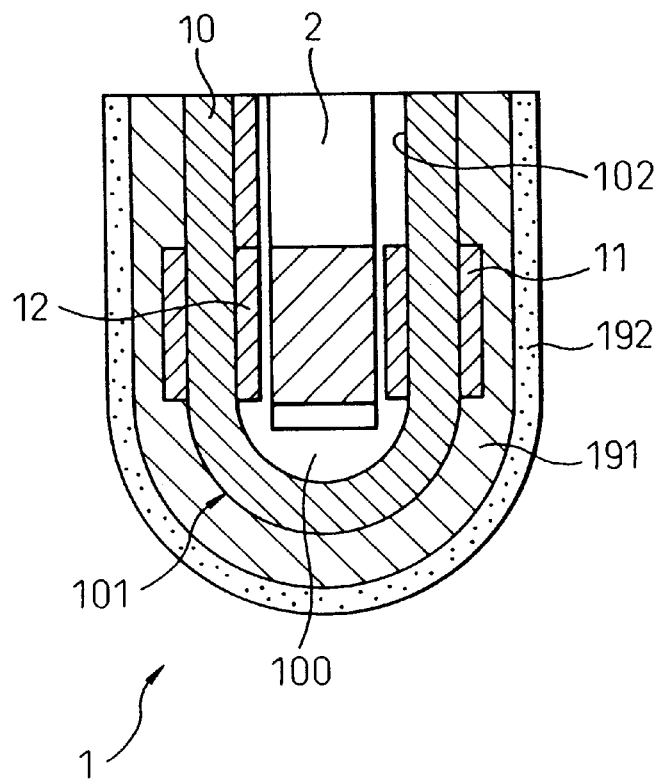
FIG. 1 is a partial cross sectional view of an oxygen sensor according to a first embodiment of the present invention.

FIG. 1 shows a detail of an oxygen sensor. A sensor element 1 is constructed by a cup shaped body 10, of a solid electrolyte, in which an air chamber 100 is formed. Furthermore, the solid electrolyte body 10 forms, at its outer surface 101, an outer electrode 11 and, at its inner surface 102, an inner electrode 12, which is in contact with the air in the air chamber 100. Furthermore, inside the air chamber 100, a heater 2 is arranged, so that the oxygen sensor element 1 is subjected to heating to an activating temperature.

An outer protection layer 191 is applied to an outer surface of the solid electrolyte body 10 so that the outside electrode 11 is covered by the protection layer 191. Finally, as the outermost layer, a toxic material trapping layer 192 is applied.

Figure 2:
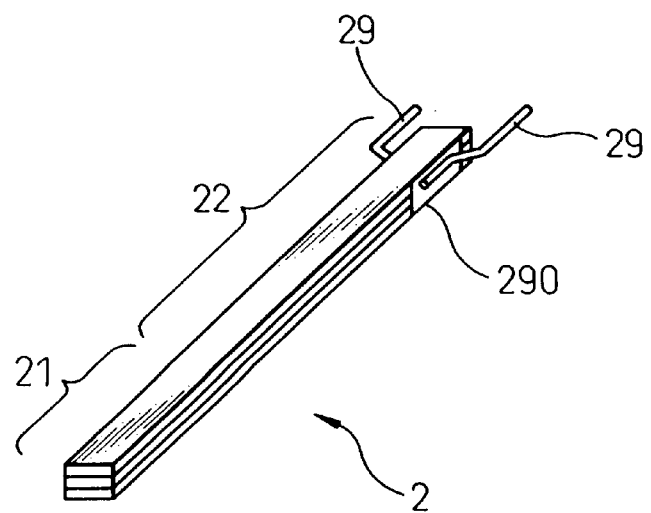
FIG. 2 is a perspective view of a heater in the oxygen sensor in FIG. 1.
Figure 3:
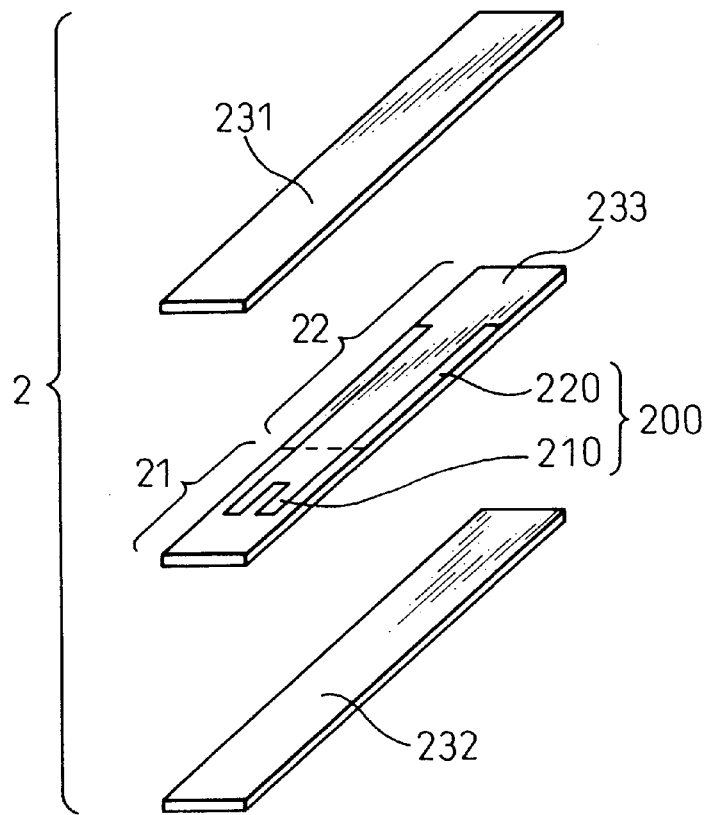
FIG. 3 is a exploded view of the heater in FIG. 2.
Figure 4:
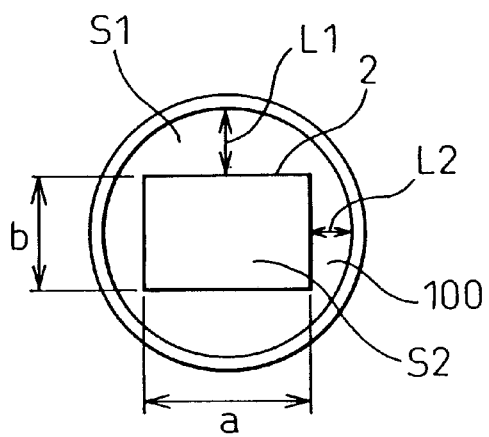
FIG. 4 is a cross sectional view of the oxygen sensor in FIG. 1.

As shown in FIGS. 2 and 3, the heater 2 is constructed by a heat generating part 21 in which a heat generating element 210 and a supporting part 22 for supporting the heat generating element 210 are housed. A lead element 220, which is in an electrical connection with the heat generating element 210, is formed on the supporting part 22. The heater 2 is of an rectangular cross sectional shape. Furthermore, the heater 2 has the same value of the cross sectional area between the heat generating part 21 and the supporting part 22. In other words, the cross sectional area Sh of the heater 2 at the heat generating part 21 and the cross sectional area Ss of the heater 2 at the supporting part 22 have the same value. Furthermore, as shown in FIG. 4, in the rectangular shape at the cross section of the heater 2, between the length a and the width b, a relationship of b/a=0.6 is obtained.

Next, a method for producing the heater 2 will be explained with reference to FIGS. 6 and 7. First, a green sheet 293 of a ceramic material is prepared. Then, a heater layer of a predetermined pattern 280 of equally spaced elongated parallel sections, is printed on the ceramic green sheet 293. Then, to the ceramic sheet 293 on which the pattern 280 is printed, from the opposite sides thereof, further ceramic green sheets 291 and 292 are applied so that a laminated body 271 (FIG. 7(a)) is obtained.

Then, as shown in FIG. 7(a), the laminated body 271 is subjected, along a line parallel to the length of a section of the pattern 280 in FIG. 6, to a cutting so that an elongated intermediate body 272 including a section of the heater pattern 280 is obtained. Then, the intermediate body 272 is subjected to a firing process, which is followed by an application of lead mounting parts 290. Finally, lead wires 29 are connected to the lead mounting parts 290, thereby providing a completed heater 2.

The heater 2 as obtained above is housed in the air chamber 100 in FIG. 1. As already explained with reference to FIGS. 1 to 4, the heater is constructed by the heat generating element 210 which, when energized, generates a heat and a lead element 220 which applies an electric voltage to the heat generating element 210. The portion in which the heat generating element is housed is a heat generating portion 21. The arrangement of the heater 2 in the air chamber 100 is such that the heat generating part 21 faces the inner electrode 12.

As shown in FIG. 3, the heater 2 is constructed as a three layer structure, which is constructed by two ceramic plates 231 and 232 and a heater plate 233, which is arranged between the ceramic plates 231 and 232 and which is provided with a patterned heater 200 constructed by the heat generating element 210 and the lead element 220. The ceramic plate 231 and 232 and the heater plate 233 are made of $Al_2O_3$. The patterned heater 200, which is constructed by the heat generating element 210 and the lead element 220, is made from tungsten-rhenium (W—Re).

As shown in FIG. 4, the rectangular shape of the heat generating part 21 of the heater 2 has a long side a of a length of 2.8 mm and a short side b of a length of 1.6 mm. Furthermore, in a state that the heater 2 is arranged in the air chamber 100, a distance $L_1$ between the long side and the inner surface 102 of the air chamber 100 is 0.8 mm and a distance $L_2$ between the short side and the inner surface 102 of the air chamber 100 is 0.4 mm. Furthermore, the cross sectional area of the heater 2 is identical between the heat generating part 21 and the supporting part 22 and is equal to 4.48 $mm^2$.

The method for producing the heater according to present invention will explained in more detail. As the first stage, ceramic green sheets 291, 292 and 293 (FIG. 7) made of $Al_2O_3$ are prepared. Then, to the green sheet 293, a layer of an electric conductive paste made of a powdered tungsten is printed at a predetermined pattern 280 of five equally spaced elongated heater sections as shown in FIG. 6. Then, to the green sheet 293 on which the pattern 280 is printed, from the opposite sides, the green sheets 291 and 292 are applied, so that the laminated body 271 as shown in FIG. 7(a) is obtained.

Then, the laminated body 271 is subjected to a drying process. Then, as shown in FIG. 7(b), the laminated body 271 is subjected to cutting so that an intermediate body 272 is separated in a manner that the intermediate body 272 includes only one heater pattern 280.

Then, the intermediate body 272 is subjected to a firing process at a temperature in a range between 1400 to 1500° C.

After the completion of the firing process, to the sides of the intermediate body 272 where the heater pattern 280 is exposed, a paste of tungsten is coated and is fired. Then, soldering of the lead wires 29 is done in a high temperature furnace of a range of a temperature between 950 to 1000° C. while using a soldering material such as the one based on Au-Cu.

As a result, the heater according to present invention as shown in FIG. 7(c) is obtained.

Now, the advantages of the heater 2 according to present invention will be explained. In the heater arranged in the air chamber 100 of the oxygen sensor element 1, the cross sectional area Sh of the heat generating part 21 and the cross sectional area Ss of the supporting part 22 are identical. On the other hand, introduction of the air into the air chamber 100 is done at the upper end of the chamber 100. According to the present invention, a quick introduction of the air is realized when the heater 2 is arranged in the air chamber 100 due to the fact that the cross sectional area of the supporting part 22 located upstream from the heat generating part 21 is equal to the cross sectional area of the heat generating part 21. As a result, even in a situation that pumping of the oxygen at an increased rate via the solid electrolyte body 10 is needed due to an especially reduced density of the oxygen, the air chamber 100 is prevented from lacking in oxygen. Thus, the sensor element 1 according to present invention allows the oxygen density to be correctly detected.

Furthermore, according to the present invention, as shown by the shaded area in FIG. 5(b), the cross sectional shape of the heater 2 is a rectangular shape, which is compared with the prior art where the cross sectional shape of the heater 9 is a circular shape, as shown by a shaded area in FIG. 5(a). In order to allow the heater to be inserted to the air chamber 100 of a fixed inner diameter, the area of a rectangular cross sectional shape of the heater in the present invention is smaller than the area of a circular cross sectional shape of the heater in the prior art. As a result, an amount of the air, which contacts with the upper end of the heater 2, is reduced, thereby reducing a loss of heat to the atmosphere. Thus, the heater 2 can effectively heat the oxygen sensor element 1. Thus, the oxygen sensor element 1 according to present invention can produce an increased speed of heating of the sensor 2.

Furthermore, according to present invention, in the rectangular shaped cross section of the heater, between the length of the long side a and the short side b, a relationship of b/a=0.57 is obtained. Thus, a desired clearance is maintained between the outer surface of the heater and the inner surface of the air chamber 100, which allows a desired amount of air to be introduced into the chamber 100. Furthermore, according to the construction of the heater 2 of the present invention, a loss of heat to the atmospheric air is reduced, which also assists in increasing the speed of the increase in the temperature of the sensor. Furthermore, in the method for producing the sensor according to present invention, a large number of heaters 2 can be simultaneously produced, thereby increasing the production efficiency as well as reducing the production cost.

In short, according to the first embodiment of the resent invention, it is possible to provide an oxygen sensor element having a heater with an increased speed of a temperature increase as well as providing a sufficient amount of introduced air into an air chamber and a method for producing such a heater at an increased efficiency.

Second Embodiment

A second embodiment of the present invention shown in FIG. 8 is related to a relationship between the aspect ratio b/a (ratio of the length of the short side to the length of the long side) and the temperature increase speed characteristic of the oxygen sensor element 1. The construction of the oxygen sensor element 1 and the method of producing it are identical with those in the first embodiment. However, the range of the values of a and b in the shape of the heater is different.

A DC voltage of 8 V is applied to the leads of the heater of the sensor in atmospheric air at room temperature, while a measurement of the speed of the increase in the temperature of the heater is done. The result is shown in FIG. 8. In FIG. 8, an ordinate in the left-handed side shows a time for causing the heater to obtain a temperature of 300° C. from the commencement of the heating by the heater. An ordinate in the right-handed side is the cross sectional area of the air chamber 100 of the oxygen sensor element minus the cross sectional area of the heat at the heat generating part 21, which corresponds to the cross sectional area of the air gap in the air chamber 100. The cross sectional area of the air chamber is measured at a location faced with the heat generating part 21 of the oxygen sensor element 1. The abscissa shows a value of the aspect ratio b/a.

In FIG. 8, when the aspect ratio b/a is increased to a value of around 0.7, the time for causing the temperature of the heater to be increased to 300° C. is prolonged.

On the other hand, the smaller the value of the ratio b/a, the shorter is the time for increasing the temperature of the heater to 300° C. However, the smaller e value of the aspect ratio, the larger is the clearance between the inner surface of the air chamber of the oxygen sensor element 1 and the heater, which causes the size of the oxygen sensor element 1 to be increased, which makes it difficult for the sensor to be arranged in a limited space. Furthermore, the smaller value of the aspect ratio causes the oxygen sensor element to be in the shape of a thin plate, which may cause the mechanical strength of the heater to be decreased, which makes the sensor not practically applicable.

In view of the above, the inventor has found that the value of the aspect ration b/a should be in a range between 0.3 and 0.7 ($0.3 \leq b/a \leq 0.7$).

Third Embodiment

The embodiment is concerned with a desired range of a ratio L1 to L2 with respect to a heat increasing characteristic of the oxygen sensor, where L1 is the distance of the long side a of the heat generating part 21 from the inner surface of the air chamber 100 and L2 is the distance of the short side b of the heat generating part 21 from the inner surface of the air chamber 100. Such a relationship between the distance ratio L1/L2 and the heat increasing characteristic is shown in FIG. 9.

According to this embodiment, the construction of the oxygen sensor and the method for producing the same are identical to those explained in the first embodiment. The only a difference is the values of L1 and L2, which are distances to the inner surface of the air chamber along the long side a and the short side b, respectively, of the heat generating part.

In FIG. 9, the ordinate on the left-handed side shows a time to an increase to a temperature of 300° C. of the oxygen sensor element, while the ordinate on the right-handed side shows an area of the space in the air chamber. The abscissa shows a value of the distance ratio L1/L2.

As will be clear from FIG. 9, when the value of the distance ratio L1/L2 is smaller than 1.5, the temperature increasing speed is too slow, which causes the oxygen sensor to be impractical.

As will also be clear from FIG. 9, larger the value of the distance ratio L1/L2, shorter is the time to the temperature of 300° C. The larger value of the distance ratio L1/L2, however, causes the clearance to be unnecessarily increased between the inner surface of the air chamber of the oxygen sensor element and the heater, which makes the size of the sensor to be intolerably increased, which makes it difficult for the sensor to be arranged in a limited space. Furthermore, a larger value of the distance ratio L1/L2 causes the shape of the oxygen sensor to be thin plate shape, which may cause its mechanical strength to be reduced, which makes the sensor to be unsuitable in practical use.

In view of the above, it is desirable that the value of the distance ratio L1/L2 is in a range between 1.5 and 2.5.

Fourth Embodiment

The fourth embodiment is concerned with a desired relationship between the cross sectional area ratio S2/S1 and the temperature increasing characteristic of the oxygen sensor element, where S1 designates the cross sectional area of the gap between the inner surface of the air chamber 100 and the outer surface of the heater 2 when the heater 2 is inserted into the air chamber 100 and S2 designates the cross sectional area of the heater 2 at the heat generating part 21.

According to this embodiment, the construction of the oxygen sensor and the method for producing the same are identical to those explained in the first embodiment. The only difference is the values of S1 and S2. As to the sensor element, tests as to the temperature increasing characteristic were performed in a similar way to those in the second embodiment and the results are shown in FIG. 10.

In FIG. 10, an ordinate shows a time up to the increase in the temperature of the sensor element to 300° C., while the abscissa is the value of the ratio S2/S1.

In FIG. 10, when the value of the S2/S1 is increased to a value higher than 0.5, the temperature increase characteristic is rapidly worsened. Thus, it can be concluded that the value of the ratio S2/S1 should be in a range equal to or larger than 0.5 ($S2/S1 \leq 0.5$).

Modified Embodiments

FIGS. 11(a) to 11(d) show various shapes of the transverse cross section of the heater according to the present invention.

Figure 11:
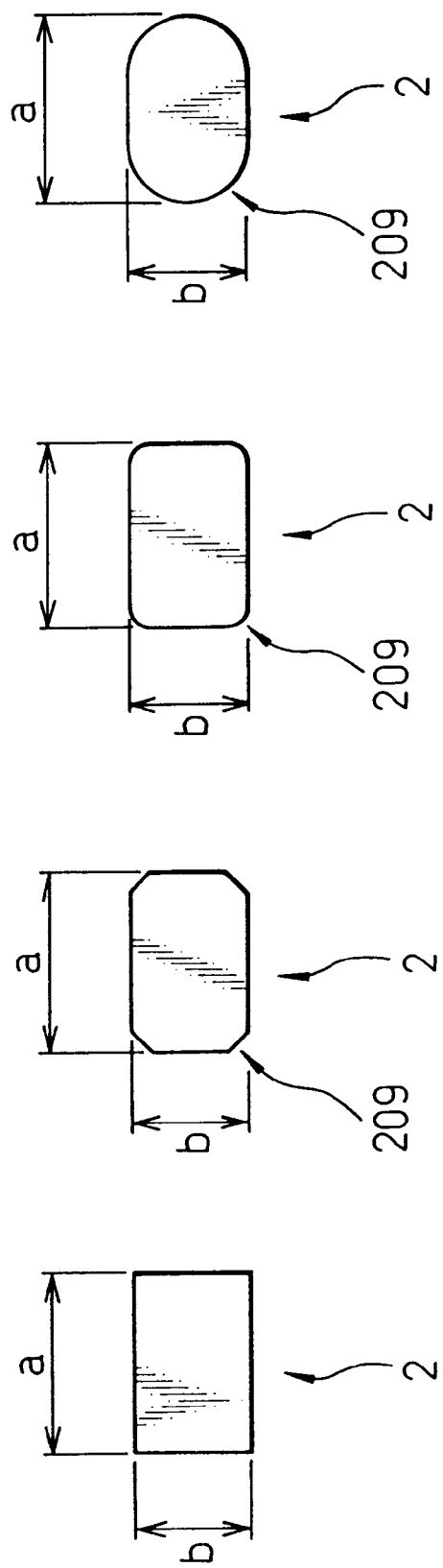

FIG. 11(a) shows a rectangular cross sectional shape with acute corners.

FIG. 11(b) shows a rectangular cross sectional shape with beveled corners.

FIG. 11(c) shows a rectangular cross sectional shape with rounded corners.

FIG. 11(d) shows a elliptic cross sectional shape.

In all of the cross sectional shapes in FIGS. 11(a) to (d), between the length of the long side a and the length of the short side b, a relationship of $0.3 \leq b/a \leq 0.7$ is maintained.

Furthermore, in order to produce the heater in each of FIGS. 11(b) to (d), the heater element is, first, produced by the same method as described with reference to the first embodiment, which is followed by a coating of a high radiation film of a thickness of 20 μm on the outer surface of the heater and a beveling at the corner portions.

The formation of the high radiation film is as follows. Namely, a slurry of ceramic powder made of $Fe_2O_3$ mixed with $Al_2O_3$ is first prepared. Then, the heater is dipped into the slurry produced by the method which is the same as that explained with reference to the first embodiment, while the heater is not yet equipped with lead wires, so that the ceramic powder is applied to the entire surface of the heater. Then, the heater with the ceramic coating is subjected to a heating and a firing at a temperature in a range 500 to 1000° C., so that a high radiation film of the ceramic is created on the surface of the heater.

The construction of the heater is identical to that in the first embodiment.

The embodiment in FIGS. 11(b) to (d) has advantages in that the heater 2 is prevented from being damaged or cracked at the corners 209 when installation of the heater 2 to the housing is performed. Furthermore, the provision of the beveled portions 209 at the corners is done by the formation of the high radiation film. Thus, as an additional advantage, the efficiency of the heat emitted to the air chamber is increased, thereby improving the oxygen sensor element in its temperature increasing speed characteristic.

In addition, the advantages as explained with reference to the first embodiment are maintained.

Further Embodiment

A further embodiment will, now, be explained with reference to FIGS. 12 to 15.

In the heater 2 shown in FIG. 12, the heater is provided with a laminated structure of ceramic plates of the same structure as explained with reference to FIGS. 1 and 3 which has a cut-out portion 291 for positioning a lead wire. In the cut-out portion 291, the lead connecting parts 290 and lead wires are arranged.

In the embodiment shown in FIG. 13, the heater 2 is, at its top end, formed with a groove 292 of a V-cross sectional shape for a positive positioning of the heater when the oxygen sensor element is used in the oxygen sensor. In more detail, as shown in FIG. 14, the sensor 3 is provided with a retaining rod 349, which is passed through an axial hole in the insulator 330. The retaining rod 349 has a top end fitted to the rubber bushing 339 and a bottom end of a V-cross sectional shape which is in an engagement with the V-cross sectional shaped groove 292 at the top end of the heater. As a result, a positive and a reliable positioning of the heater 2 is realized.

FIG. 15 illustrates an embodiment of the heater 2, where the cross sectional area of the heat generating part 21, in which the heat generating element 210 is stored, is larger than that of the supporting part 22, in which a lead element 210 is arranged. Other constructions are identical to those in the first embodiment.

The heater 2 in FIG. 12 is advantageous in that work to connect the lead wire 29 to the heater is easy, which increases the production efficiency.

The heater 2 in FIG. 13 is advantageous in that the positioning of the heater is easy.

Finally, the heater 2 in FIG. 15 is advantageous in that an increased clearance is obtained between the inner wall of the air chamber 100 and the heater 2, which allows the amount of introduced air to be increased.

We claim:

1. An oxygen sensor comprising:

a cup shaped body made of a solid electrolyte body;

an air chamber inside said solid electrolyte body, which is opened to an outside atmospheric air;

an outer electrode on an outer surface of said solid electrolyte body;

an inner electrode on an inner surface of said solid electrolyte body, and;

a heater including a heat generating part in which a heat generating element is stored and a supporting part for supporting the heat generating portion, the supporting part having a lead element which is electrically connected to the heat generating element, at least a portion of the heater positioned in the cup shaped body;

a relationship between the cross sectional area Sh of the heat generating part and the cross sectional area Ss of said supporting part being such that $Sh \geq Ss$;

a relationship between the length a of the long side and the length b of the short side of a rectangular cross sectional shape of the heater at the heat generating part being such that $0.3 \leq b/a \leq 0.7$.

2. An oxygen sensor according to claim 1, wherein said heater is beveled at the corners of its rectangular cross section.

3. An oxygen sensor according to claim 1, wherein, said heater has, at its outer surface, a coating of a high radiation film made of at least one of materials selected from $Fe_2O_3$, NiO, $Y_2O_3$ and $Si_3N_4$.

4. An oxygen sensor according to claim 1, wherein a relationship between a cross sectional area S1 of the space in the air chamber in which the heater is inserted and the cross sectional area S2 of the heat generating part of the heater is such that $S2/S1 \leq 0.5$.

5. An oxygen sensor comprising:

a cup shaped body made of a solid electrolyte body;

an air chamber inside said solid electrolyte body, which is opened to an outside atmospheric air;

an outer electrode on an outer surface of said solid electrolyte body;

an inner electrode on an inner surface of said solid electrolyte body, and;

a heater including a heat generating part in which a heat generating element is stored and a supporting part for supporting the heat generating portion, the supporting part having a lead element which is electrically connected to the heat generating element;

a relationship between the cross sectional area Sh of the heat generating part and the cross sectional area Ss of said supporting part being such that $Sh \geq Ss$;

a portion of the heater having a rectangular cross sectional shape having a long side and a short side;

wherein in a gap between an inner wall of the air chamber facing the heater and the heat generating part of the heater, a relationship between the distance L1 of said inner wall from the long side of the rectangular cross section and the distance L2 of said inner wall from the short side of the rectangular cross section is such that $1.5 \leq L1/L2 \leq 2.5$.

* * * * *